United States Patent [19]

Motolese

[11] Patent Number: 5,371,350

[45] Date of Patent: Dec. 6, 1994

[54] HIGHLY SENSITIVE ELECTRONIC DEVICE FOR MEASURING EXTREMELY FAINT LIGHT EMISSIONS

[76] Inventor: Guido Motolese, Via Carroccio 12, 20123 Milan, Italy

[21] Appl. No.: 93,825

[22] Filed: Jul. 20, 1993

[30] Foreign Application Priority Data

Jul. 24, 1992 [IT] Italy .............................. MI92A001815

[51] Int. Cl.⁵ ............................................. G01N 21/76
[52] U.S. Cl. ............................ 250/207; 250/361 C; 422/52
[58] Field of Search ............... 250/207, 361 C; 422/52, 422/64, 68.1, 54; 356/244; 436/172

[56] References Cited

U.S. PATENT DOCUMENTS

| | | | |
|---|---|---|---|
| 3,659,100 | 4/1972 | Anderson et al. | 250/361 C |
| 3,871,767 | 3/1975 | Holm-Hansen et al. | 350/361 C |
| 4,099,920 | 7/1978 | Heiss | 356/244 |
| 4,213,703 | 7/1980 | Haunold et al. | 422/54 |
| 4,818,883 | 4/1989 | Anderson et al. | 422/52 |
| 5,223,218 | 6/1993 | Fukuoka et al. | 422/52 |

Primary Examiner—David C. Nelms
Assistant Examiner—Stephone B. Allen
Attorney, Agent, or Firm—Guido Modiano; Albert Josif; Daniel O'Byrne

[57] ABSTRACT

An electronic device for measuring extremely faint light emissions comprises a photomultiplier tube surrounded by a sleeve made of a material which is a good heat conductor, cooled to a low temperature and insulated from the outside, a thermally insulating and optically transparent lightguide body being stably glued to the photocathode of the photomultiplier tube to receive the light radiation emitted by a specimen to be examined, which is inserted in a cavity of a supporting structure holding a rotary body which can be turned in front of the lightguide body, so as to operate as a shutter for the lightguide in a first turned measurement position thereof to allow measurement of the dark signal and then allow, as the rotary body and the specimen held therein are turned to a second measurement position, to measure the light emission from the specimen.

5 Claims, 1 Drawing Sheet

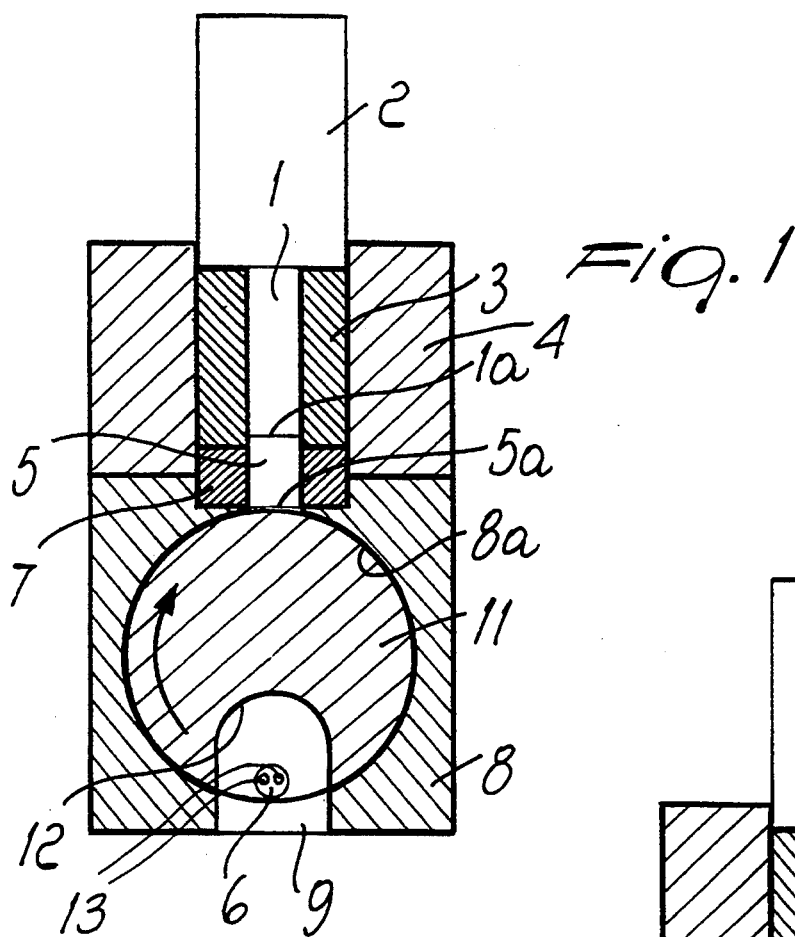
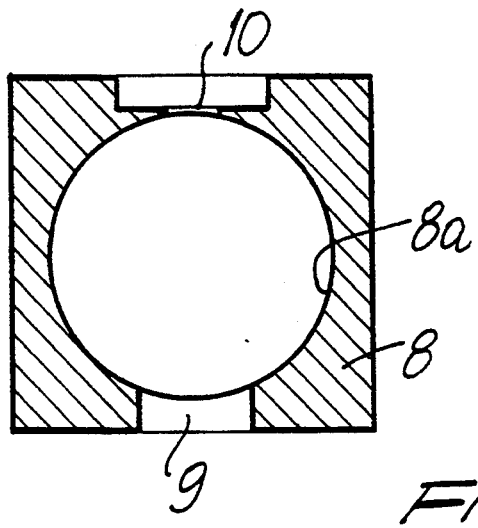
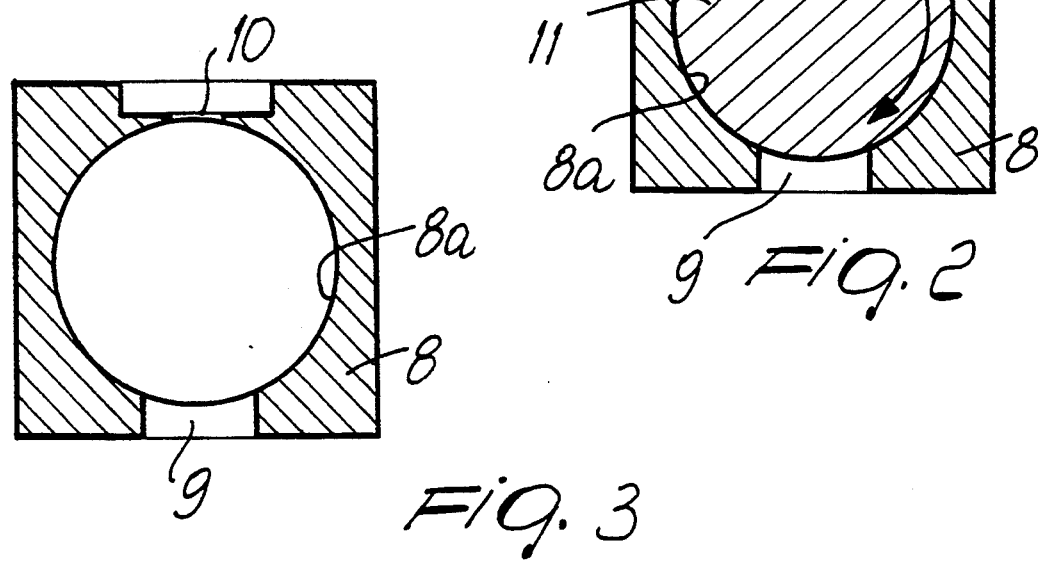

HIGHLY SENSITIVE ELECTRONIC DEVICE FOR MEASURING EXTREMELY FAINT LIGHT EMISSIONS

BACKGROUND OF THE INVENTION

The present invention relates to an electronic device, particularly a high-sensitivity or high-gain photometer for measuring the light emissions which are very often associated with biochemical or chemical reactions as well as with some physical phenomena.

As is known, the apparatus for detecting and measuring extremely faint light radiation, generally termed "photometer", is a highly sensitive instrument which essentially comprises an element holding the specimen to be examined, a sensor-amplifier for the signals emitted by said specimen and an electronic device for processing the signal output by said sensor-amplifier.

It is also known that a photomultiplier is often used as sensor-amplifier for low-intensity light signals; essentially, said photomultiplier is constituted by a set of electrodes, i.e. by a photocathode, a plurality of dynodes and an anode, all of which are contained in a glass vessel in which a hard vacuum, normally at a pressure of less than $10^{-6}$ torr, is formed. This kind of photomultiplier allows to achieve high amplifications which vary according to the number of dynodes and to the power supply voltage.

The most significant characteristic of a photometer is its sensitivity. In fact, the higher the sensitivity, the greater the ability of the instrument to measure very faint light emissions and thus to aid the experimenter in studying phenomena which have not yet been investigated from this point of view.

Sensitivity is generally defined according to the type of phenomenon being measured, but in any case it is ultimately dependent on the value of the lowest intensity of the phenomenon being studied which can be detected without uncertainties, i.e. with a sufficiently high signal-to-noise ratio.

Generally, the amplitude or intensity of the light signal measured by a photometer mainly depends on:

its light-gathering efficiency, which is defined as the ratio between the amount of light gathered by the sensor during a given time interval and the amount of light emitted by the specimen during the same time interval;

its light conversion efficiency, defined as the ratio between the amplitude or intensity of the signal emitted by the sensor and the amount of light received by the sensor in the given time interval.

The noise of a detector instead generally depends on phenomena which occur within the detector and on the subsequent signal processing chain.

The sensitivity of a photometer therefore ultimately depends on the ratio between the product of the two coefficients which characterize the gathering and conversion efficiency and of the intrinsic noise of the detection system.

It should also be considered that, although the measurement chamber of a photometer is kept in absolute darkness, the sensor nonetheless emits a signal even in the absence of a specimen. This signal is measured before introducing any specimen and this measurement, known as "dark signal", is then subtracted from the measurement made in the presence of the specimen in order to determine the net signal which is due to said specimen.

The sensor-amplifier is therefore the essential element of a photometer, and its design conditions the light conversion efficiency.

Maximum light-gathering efficiency is generally obtained by designing the apparatus so that the specimen can be placed as close as possible to the sensor, so that the solid angle under which the sensor "sees" the specimen is the widest possible. A considerable improvement in gathering efficiency can be obtained by using reflecting surfaces which surround the specimen and reflect toward the sensor the largest possible part of the light emitted by the specimen in other directions.

In order to achieve high sensitivity, on the other hand, attempts are made to reduce the intrinsic noise of the sensor, which is essentially thermal. A method currently used entails cooling the sensor to temperatures below the lower bend of the sensor sensitivity curve supplied by the manufacturer, which plots "dark emission" against temperature.

The solution of cooling the sensor to reduce its noise, however, forces to thermally insulate the sensor from the specimen, which usually must be kept at a different temperature which can vary according to criteria selected by the experimenter according to the phenomenon being studied, the behavior whereof is generally affected by temperature. Thermal insulation is obtained by using gates with double- or triple-glazing, with vacuum between the glass plates, so as to limit heat exchange between the space occupied by the sensor and the space occupied by the specimen exclusively to the part due to irradiation. In any case, the sensor is necessarily moved further away from the specimen, and thus the improvement in sensitivity obtained by reducing the thermal noise entails a considerable reduction of the light-gathering efficiency due, on one hand, to the significant decrease in the solid angle under which the sensor sees the specimen and, on the other hand, to multiple reflections on the surfaces of the glass plates of the insulating gate.

Maximum light-gathering efficiency and high sensitivity obtained by reducing thermal noise through sensor cooling are thus mutually contrasting and, in the current state of the art, mutually exclusive design targets.

SUMMARY OF THE INVENTION

Therefore, the aim of the present invention is to provide a photometer which is designed and structured so as to eliminate, in a substantially complete manner, the drawbacks and limitations of current photometers and most of all is capable of allowing extremely high sensitivity and high light-gathering efficiency without causing any reduction in the solid angle between the specimen and the sensor.

Another object of the present invention is to provide a photometer of the above specified type which is structured so as to avoid the use of any moving shutter or the like for the measurement gate or window in order to allow measurement of the "dark signal" and then measurement of the light radiation emitted by the specimen.

A further object is to provide a photometer which is highly reliable and structurally simple and has a competitive cost with respect to that of current photometers.

This aim, these objects and others which will become apparent from the following description are achieved by an electronic device for measuring extremely faint light radiation emitted during biochemical and chemical reactions according to the main claim.

More particularly, said body acting as lightguide is block-shaped and is anchored to the photocathode of said photomultiplier by glueing it by means of a material having a refraction index which is very close to that of said lightguide and of the gate constituted by the base of said photocathode, so as to avoid losses by reflection on the separation surfaces of the mutually coupled bodies.

Said photocathode is furthermore preferably made of semitransparent material and is thermally insulated.

BRIEF DESCRIPTION OF THE DRAWINGS

Further characteristics and advantages of the present invention will become apparent from the following description, given by way of non-limitative example with reference to the accompanying drawing, wherein:

FIG. 1 is a schematic view of the measurement device or photometer, built according to the present invention and shown in the position for measuring the dark signal;

FIG. 2 is a view of the same device as shown in FIG. 1, in the position for measuring the signal emitted by the specimen being examined; and FIG. 3 is a view of the fixed part of the cylindrical specimen holder facing the gate or window of the photomultiplier.

DESCRIPTION OF THE PREFERRED EMBODIMENTS

With reference to the above figures, the electronic device which constitutes the improved photometer according to the present invention uses the main components of a known photometer, which comprise, in the present embodiment, a photomultiplier tube associated with an electronic device for processing the signal emitted by said photomultiplier. Means for detecting the light emitted by a specimen to be examined are associated with these two components and are structured so as to give the photometer extremely high sensitivity together with a high light emission conversion efficiency.

More precisely, the photometer according to the present invention comprises by a photomultiplier tube 1 connected to an electronic processor 2 for processing the signal output by the photomultiplier 1.

The sensitive outer surface of the photomultiplier is accommodated within a sleeve 3 made of a material having a good thermal conductivity and is cooled to approximately −20°, the cooling sleeve 3 being separated from the environment by a second sleeve 4 which is made of a thermally insulating material.

A transparent body or lightguide 5 is bound to the photocathode 1a by glueing and acts as lightguide for the light radiation emitted by the specimen being examined, as better specified hereinafter; said specimen is contained in a test tube or the like, designated by the reference numeral 6 in the figures.

Said lightguide 5 is made of a thermally insulating but optically transparent material, so that the sensitive surface of the photomultiplier optically contacts the specimen 6. Glueing by means of a material having a refraction index very close to that of the lightguide 5 and of the gate of the photomultiplier 1 avoids losses by reflection on the separation surfaces of the various media, so that the only loss due to reflection occurs at the inlet surface 5a of the lightguide, i.e. on a single surface, as would occur if the photomultiplier were in direct contact with the specimen. However, with this geometrical arrangement, the solid angle under which the specimen sees the photomultiplier is the solid angle under which the specimen sees the inlet surface of the lightguide, whereas losses due to absorption in passing through the guide are irrelevant. Said lightguide 5 is furthermore insulated from the outside and from the specimen 6 by a thermally insulating material sleeve 7.

A specimen holder furthermore stably faces said lightguide 5, said holder including a prism-shaped support 8 (FIG. 3) inside which a cylindrical cavity 8a is formed; the axis of said cavity is at right angles to the photomultiplier-lightguide assembly, and the cavity has, at the bottom thereof, an opening 9 for the insertion of the specimen 6 and, at a diametrically opposite top position, an opening or window 10 which stably faces the lightguide inlet surface 5a. A rotatable solid cylindrical body 11 is furthermore engaged in said cylindrical cavity 8a and is provided with a peripheral cavity 12 which accommodates the test tube with the specimen 6 to be examined.

This embodiment allows the external cylindrical surface of the cylinder 11 to stay facing, and almost make contact with, the inlet surface 5a of the lightguide 5, so that the surface itself of the solid cylinder 11 acts as shutter of the inlet surface 5a of the lightguide 5 and thus of the photomultiplier to allow the detection of the dark signal prior to the measurement of the signal emitted by the specimen. In fact, by rotating the cylinder 11, its opaque cylindrical surface, which has acted as shutter, is then replaced in front of the inlet surface 5a of the lightguide 5 by the specimen 6, which thus directly faces the photomultiplier 1 with no interposition of spaces which would negatively affect the measurement since they would increase the distance of the specimen from the optical sensor.

Therefore, the adopted constructive solution entails the advantage that the photomultiplier tube is always intrinsically protected from ambient light in any operating condition.

Also according to the present invention, all the regions which cooperate with the photomultiplier tube, and in any case all those which can be seen by said photomultiplier tube, are made of materials which are neither phosphorescent nor luminescent, so as to prevent the emitted signals from being contaminated by photons emitted by said materials.

Furthermore, the photometer described above is provided with means, substantially syringe needles or the like, designated by the reference numeral 13 in the figures, which allow the addition of reagents to the specimen, and with mechanical means which cause the test tube that holds the specimen 6 to vibrate and/or oscillate and allow measurements of the luminescent emissions in the dark and in the presence of the sensor from the very beginning of the reaction.

The above described photometer is furthermore provided with conventional kinematic means for rotating and stopping the specimen-holder cylinder and with equally known means for cooling the sleeves which enclose the photomultiplier and the lightguide.

Finally, it is obvious that the invention as described above according to a possible and preferred embodiment thereof is susceptible to structurally and functionally equivalent modifications and variations without abandoning the protective scope of said invention.

I claim:

1. An electronic device for measuring extremely faint light radiation emitted during biochemical and chemical reactions and physical phenomena, of a type including a sensor-photomultiplier, a device for holding a specimen to be examined and an electronic processor for processing a signal output from said sensor-photomultiplier, wherein said electronic device comprises a photomultiplier tube having a photocathode encompassed by a good thermal conductive material sleeve thermally insulated with respect to an outside environment and cooled to a set low temperature, a transparent thermally insulating body operating as a lightguide being glued to said photocathode to receive a light radiation from said specimen, said device for holding said specimen including a prism-shaped support having a cylindrical cavity in which a solid rotary cylindrical body is rotatably housed, said body being provided with a peripheral cavity for housing a test tube holding said specimen, said cylindrical body having an opaque outer cylindrical surface portion acting as a shutter for light sent through said lightguide body to allow measurement of a dark signal with said rotary cylindrical body turned to a first measurement position and measurement of a light emission with said rotary cylindrical body turned to a second measurement position.

2. An electronic device according to claim 1, wherein said body acting as a lightguide is anchored to the photocathode of said photomultiplier tube by a glue having a refraction index close to that of said lightguide and of a window portion of the photomultiplier.

3. An electronic device according to claim 1, wherein said cavity is provided with at least two peripheral openings, one of said openings defining a window for measuring radiation from said specimen, the other opening being provided for introducing said specimen in said cavity.

4. An electronic device according to claim 1, wherein said device comprises a plurality of constructional parts adapted to be exposed to said photomultiplier tube, said parts being made of materials which are neither fluorescent nor luminescent.

5. An electronic device according to claim 1, wherein said device further comprises supplying means to allow an addition of reagents to the specimen being examined and mechanical means for mixing said reagents.

* * * * *